(12) United States Patent
Etcheverry et al.

(10) Patent No.: US 10,846,875 B2
(45) Date of Patent: Nov. 24, 2020

(54) ADAPTIVE NONLINEAR OPTIMIZATION OF SHAPE PARAMETERS FOR OBJECT LOCALIZATION IN 3D MEDICAL IMAGES

(71) Applicant: Siemens Healthcare GmbH, Erlangen (DE)

(72) Inventors: Mayalen Irene Catherine Etcheverry, Lawrenceville, NJ (US); Bogdan Georgescu, Plainsboro, NJ (US); Sasa Grbic, Plainsboro, NJ (US); Dorin Comaniciu, Princeton Junction, NJ (US); Benjamin L. Odry, West New York, NJ (US); Thomas Re, Monroe, NJ (US); Shivam Kaushik, South Amboy, NJ (US); Bernhard Geiger, Cranbury, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 82 days.

(21) Appl. No.: 16/270,918

(22) Filed: Feb. 8, 2019

(65) Prior Publication Data
US 2019/0378291 A1 Dec. 12, 2019

Related U.S. Application Data

(60) Provisional application No. 62/681,865, filed on Jun. 7, 2018.

(51) Int. Cl.
*G06T 7/70* (2017.01)
*G06T 3/20* (2006.01)
(Continued)

(52) U.S. Cl.
CPC .............. *G06T 7/70* (2017.01); *G06N 20/10* (2019.01); *G06T 3/20* (2013.01); *G06T 3/40* (2013.01);
(Continued)

(58) Field of Classification Search
CPC .... G06T 7/70; G06T 3/20; G06T 3/40; G06T 3/60; G06T 2207/20021;
(Continued)

(56) References Cited

U.S. PATENT DOCUMENTS 9,569,736 B1   2/2017 Ghesu et al.
9,792,531 B2  10/2017 Georgescu et al.
(Continued)

FOREIGN PATENT DOCUMENTS

WO   WO2018015414 A1   1/2018

OTHER PUBLICATIONS

Extended European Search Report (EESR) dated Sep. 10, 2019 in corresponding European Patent Application No. 19177891.9.
(Continued)

*Primary Examiner* — Ming Y Hon

(57) ABSTRACT

System and methods are provided for localizing a target object in a medical image. The medical image is discretized into a plurality of images having different resolutions. For each respective image of the plurality of images, starting from a first image and progressing to a last image with the progression increasing in resolution, a sequence of actions is performed for modifying parameters of a target object in the respective image. The parameters of the target object comprise nonlinear parameters of the target object. The sequence of actions is determined by an artificial intelligence agent trained for a resolution of the respective image to optimize a reward function. The target object is localized in the
(Continued)

medical image based on the modified parameters of the target object in the last image.

20 Claims, 8 Drawing Sheets

(51) Int. Cl.
  *G06T 3/40* (2006.01)
  *G06T 3/60* (2006.01)
  *G16H 30/40* (2018.01)
  *G06N 20/10* (2019.01)

(52) U.S. Cl.
  CPC .............. *G06T 3/60* (2013.01); *G16H 30/40* (2018.01); *G06T 2207/20021* (2013.01); *G06T 2207/20081* (2013.01); *G06T 2207/30004* (2013.01)

(58) Field of Classification Search
  CPC . G06T 2207/20081; G06T 2207/30004; G06T 2207/20084; G06T 7/0012; G16H 30/40; G06N 20/10
  See application file for complete search history.

(56) References Cited

U.S. PATENT DOCUMENTS

| | | | | |
|---|---|---|---|---|
| 10,417,556 | B1* | 9/2019 | Fairbank | G06N 3/006 |
| 2008/0101676 | A1* | 5/2008 | Zheng | A61B 6/503 |
| | | | | 382/131 |
| 2011/0222750 | A1* | 9/2011 | Liao | A61B 6/503 |
| | | | | 382/131 |
| 2014/0270374 | A1* | 9/2014 | Unzueta | G06K 9/00248 |
| | | | | 382/103 |
| 2016/0034780 | A1* | 2/2016 | Duan | G06K 9/4619 |
| | | | | 382/195 |
| 2017/0116497 | A1* | 4/2017 | Georgescu | A61B 8/5223 |
| 2018/0005083 | A1 | 1/2018 | Georgescu et al. | |
| 2019/0236411 | A1* | 8/2019 | Zhu | G06K 9/6292 |
| 2019/0311478 | A1* | 10/2019 | Avendi | G06K 9/726 |

OTHER PUBLICATIONS

Ghesu, et al.; Robust Multi-scale Anatomical Landmark Detection in Incomplete 3D-CT Data; 2017; pp. 194-202. Springer, Cham.

Etcheverry Mayalen et al.: "Nonlinear Adaptively Learned Optimization for Object Localization in 3D Medical Images"; Sep. 20, 2018 (Sep. 20, 2018); International Conference on Computer Analysis of Images and Patterns. CAIP 2017: Computer Analysis of Images and Patterns; [Lecture Notes in Computer Science; Lect. Notes Computer], Springer, Berlin, Heidelberg, pp. 254-262.

Ranjan et al., "Organ Localization through Anatomy-Aware Non-Rigid Registration with Atlas", Applied Imagery Pattern Recognition Workshop, 2011, IEEE, pp. 1-5.

Criminisi, et al. "Regression forests for efficient anatomy detection and localization in CT studies." International MICCAI Workshop on Medical Computer Vision. Springer, Berlin, Heidelberg, 2010.

Cuingnet et al., "Automatic Detection and Segmentation of Kidneys in 3D CT Images Using Random Forests", International Conference on Medical Image Computing and Computer-Assisted Intervention, Springer, Berlin, Jan. 22, 2014, 9 pgs.

Zheng et al., "Marginal Space Learning for Efficient Detection of 2D/3D Anatomical Structures in Medical Images", International Conference on Information Processing in Medical Images, Springer, Berlin, 2009, 12 pgs.

Ghesu et al., "Marginal Space Deep Learning: Efficient Architecture for Volumetric Image Parsing", IEEE Transactions on Medical Imaging, 2016, 13 pgs.

Ghesu et al., "Multi-Scale Deep Reinforcement Learning for Real-Time 3D-Landmark Detection in CT Scans" IEEE Transactions on Pattern Analysis and Machine Intelligence, 2017, 14 pgs.

Mnih et al., "Playing Atari with Deep Reinforcement Learning", 2013, arXiv:1312.5602, 9 pgs.

Van Hasselt et al., "Deep Reinforcement Learning with Double Q-Learning", AAAI, vol. 16, 2016, 12 pgs.

Ren et al., "Faster R-CNN: Towards Real-Time Object Detection with Region Proposed Networks", Convolutional Neural Network, Jan. 6, 2016, 14 pgs.

Akselrod-Ballin et al., A Region Based Convolutional Network for Tumor Detection and Classification in Breast Mammography; Deep Learning and Data Labeling for Medical Applications, Springer, 2016, pp. 197-205.

Chen et al., "Automatic Alignment of Brain MR Scout Scans Using Data-adaptive Multi-structural Model", MICCAI, 2011, Part II, Springer-Verlag, Berlin, pp. 574-581.

Zheng et al., "Fast Automatic Heart Chamber Segmentation from 3D CT Data Using Marginal Space Learning and Steerable Features", IEEE ICCV, 2007, 8 pgs.

Ghesu et al., "Toward Intelligent Robust Detection of Anatomical Structures in Incomplete Volumetric Data", Medical Image Analysis, vol. 48, Aug. 2018, pp. 203-213.

* cited by examiner

Discretize a medical image into a plurality of images having different resolutions, the medical image comprising a target object
302

For each respective image of the plurality of images, starting from a first image and progressing to a last image with the progression increasing in resolution, perform a sequence of actions for modifying parameters of the target object in the respective image
304

Localize the target object in the medical image based on the modified parameters of the target object
306

Output results of the localization of the target object from the medical image
308

|  | Inter-rater | Landmark-based | Inventive approach (4mm) | (2mm) |
|---|---|---|---|---|
| $\alpha_1(°)$ | 0.99(≤3.50) | 0.92(≤3.45) | 1.28(≤3.78) | 0.92(≤3.23) |
| $\alpha_2(°)$ | 1.04(≤4.71) | 0.99(≤4.93) | 1.20(≤4.46) | 0.97(≤2.11) |
| $\beta_1(°)$ | 1.47(≤5.19) | 2.00(≤6.86) | 1.62(≤6.35) | 1.39(≤5.86) |
| $\delta_R(mm)$ | 1.32(≤3.54) | 2.06(≤5.78) | 2.65(≤7.54) | 1.45(≤3.30) |
| $\delta_L(mm)$ | 1.45(≤4.75) | 1.89(≤5.03) | 2.20(≤8.68) | 1.83(≤4.95) |
| $\delta_A(mm)$ | 2.00(≤3.36) | 1.65(≤4.93) | 2.46(≤6.07) | 1.94(≤6.08) |
| $\delta_P(mm)$ | 1.48(≤3.89) | 1.86(≤9.62) | 3.31(≤9.68) | 1.65(≤5.68) |
| $\delta_I(mm)$ | 3.33(≤3.61) | 2.22(≤6.00) | 3.12(≤11.5) | 2.74(≤8.21) |
| $\delta_S(mm)$ | 1.3(≤3.28) | 2.13(≤5.74) | 3.04(≤7.46) | 2.16(≤6.31) |

ADAPTIVE NONLINEAR OPTIMIZATION OF SHAPE PARAMETERS FOR OBJECT LOCALIZATION IN 3D MEDICAL IMAGES

CROSS-REFERENCE TO RELATED APPLICATIONS

This application claims the benefit of U.S. Provisional Application No. 62/681,865, filed Jun. 7, 2018, the disclosure of which is incorporated herein by reference in its entirety.

TECHNICAL FIELD

The present invention relates generally to object localization in 3D medical images, and more particularly to adaptive nonlinear optimization of shape parameters for object localization in 3D medical images using reinforcement learning based methods.

BACKGROUND

Localization of an anatomical structure refers to the task of determining a region in a medical image that contains the anatomical structure. Localization of anatomical structures in medical images is an important prerequisite for subsequent medical image analysis tasks, such as medical image registration, volumetric organ segmentation, lesion quantification, and abnormality detection. However, localization of anatomical structures in medical images is challenging due to the variability of the input data that may arise as a result of different anatomy sizes, image orientations, field-of-views, slicing, and patient positioning.

Conventional approaches for localization of anatomical structures in medical images all have drawbacks. For example, atlas-based registration methods for object localization requires complex non-rigid registration and are not scalable to large three-dimensional volumes. Regression-based methods for object localization learn the non-linear mapping from voxels to parameters by formulating the localization as a multivariate regression problem. However, such regression-based methods are difficult to train, especially where the dataset has a large variation in the field of view, limiting their applicability in three-dimensional medical imaging. Classification-based methods typically perform object localization by discretizing the parametric space in a large set of hypotheses and testing through a trained classifier, however such classification-based methods imposes dependencies in the parametric search space, which can lead to suboptimal solutions and is hard to generalize. Region-based convolutional neural networks (R-CNN) based techniques for medical image analysis requires very large annotated datasets to train and is difficult to generalize for a variety of clinical cases.

Recently, deep-reinforcement learning was proposed for landmark detection in medical images. In U.S. Pat. No. 9,792,531, titled "Intelligent Multi-Scale Medical Image Landmark Detection," incorporated herein by reference in its entirety, an artificial intelligence agent is described for navigating through three target parameter dimensions (x, y, z) of a linear parametric space for landmark detection in medical images using deep reinforcement learning. However, the agent is limited to navigating in three parametric dimensions, and is not able to parameterize a target object according to nonlinear parameters, such as, e.g., rotation, shear, and scale. Accordingly, such an agent is not suitable for many image analysis applications.

BRIEF SUMMARY OF THE INVENTION

In accordance with one or more embodiments, system and methods are provided for localizing a target object in a medical image. The medical image is discretized into a plurality of images having different resolutions. For each respective image of the plurality of images, starting from a first image and progressing to a last image with the progression increasing in resolution, a sequence of actions is performed for modifying parameters of a target object in the respective image. The parameters of the target object comprise nonlinear parameters of the target object. The sequence of actions is determined by an artificial intelligence agent trained for a resolution of the respective image to optimize a reward function. The target object is localized in the medical image based on the modified parameters of the target object in the last image.

In accordance with one embodiment, the parameters of the target object comprise translation, rotation, and scaling parameters defining a nine dimensional space.

In accordance with one embodiment, the AI agent is trained using deep reinforcement learning.

In accordance with one embodiment, the sequence of actions comprise a stop action in which the parameters of the target object are unchanged.

In accordance with one embodiment, the sequence of actions comprise a stop action in which the parameters of the target object are unchanged. The sequence of actions may be performed by repeatedly performing an action for modifying the parameters of the target object for a current state in the respective image that optimizes the reward function learned by the AI agent trained for the resolution of the respective image until a stopping condition is satisfied. The stopping condition comprises one of a stop action determined by the AI agent, a predetermined number of steps, and consecutive complementary actions. The modified parameters of the target object in the respective image may be used as initial parameters for the target object in a next image of the plurality of images. The target object may be an anatomical landmark.

These and other advantages of the invention will be apparent to those of ordinary skill in the art by reference to the following detailed description and the accompanying drawings.

BRIEF DESCRIPTION OF THE DRAWINGS

FIG. 3 shows a method for localizing a target object in a medical image, in accordance with one or more embodiments;

FIG. 6 shows a table comparing embodiments of the present invention with conventional methods;

DETAILED DESCRIPTION

The present invention generally relates to methods and systems for nonlinear adaptively learned optimization for object location in 3D medical images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed by a computer system using data stored within the computer system.

It should be understood that while embodiments discussed herein may be discussed with respect to the localization of anatomical objects in medical images, the present invention is not so limited. Embodiments of the present invention may be applied for the localization of any object in any image.

Figure 1:
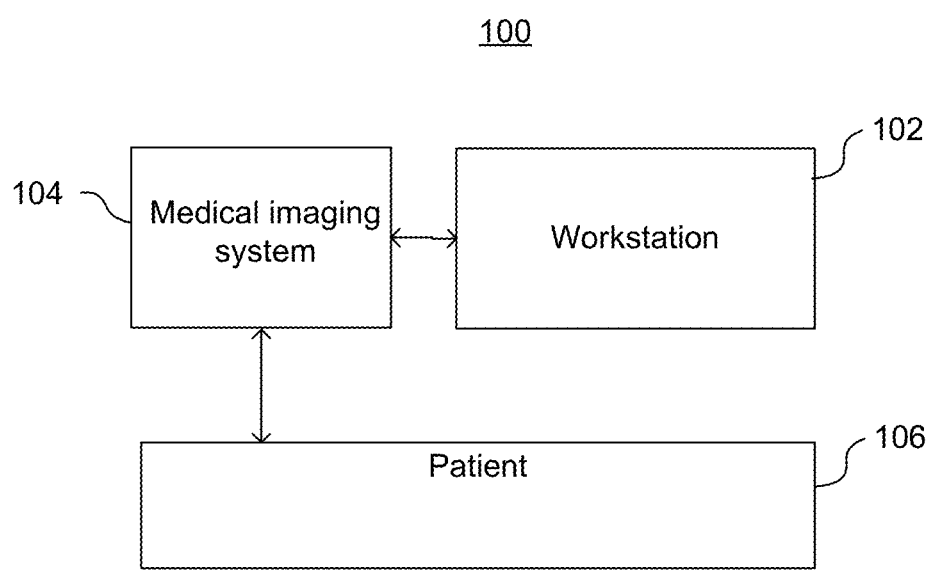
FIG. 1 shows an illustrative system for localizing a target object in a medical image, in accordance with one or more embodiments.

FIG. 1 shows a system 100 configured for localization of an anatomical object in a medical image, in accordance with one or more embodiments. System 100 includes workstation 102, which may be used for assisting a clinician (e.g., a doctor, a medical professional, or any other user) in performing a medical evaluation on a patient 106 (or any other subject). Workstation 102 may be implemented using any suitable computing device, such as, e.g., computer 802 of FIG. 8.

In one embodiment, workstation 102 may assist the clinician in performing a medical evaluation of patient 106 based on medical images received from one or more medical imaging systems 104. In an advantageous embodiment, the medical images received from medical imaging system 104 is a three-dimensional (3D) medical image. However, it should be understood that the medical images received from medical imaging system 104 may be any type of image of any suitable modality or domain. For example, the medical images received from medical imaging system 104 may be, e.g., a two-dimensional (2D) or 3D computed tomography (CT), x-ray, magnetic resonance imaging (MRI), ultrasound (US), single-photon emission computed tomography (SPECT), positron emission tomography (PET), or any other suitable modality or combination of modalities. The medical images may be directly received from medical imaging system 104 or may be received by loading previously stored medical images of the patient acquired using medical imaging system 104.

Workstation 102 analyzes the medical images received from medical imaging system 104 to assist the clinician in performing the medical evaluation of patient 106. Many medical image analysis tasks, such as, e.g., image registration, organ segmentation, lesion quantification, and abnormality detection, require localization of anatomical objects.

Embodiments of the present invention provide for a deep reinforcement-learning based artificial intelligence (AI) agent trained to localize a target object in a medical image by learning a search strategy that maximizes a reward function. The trained AI agent navigates through a nonlinear multi-dimensional parametric space of the medical image to localize the target object. In one advantageous embodiment, the trained AI agent navigates a nine dimensional parametric space of the medical image to automatically estimate nine parameters of a target object: Cartesian coordinates (x, y, z) defining a center position of the target object; yaw, pitch, and roll defining an orientation of the target object, and width, depth, and height defining a scale of the target object. The estimated parameters of the target object define an anatomical bounding box providing gives the localization of the target object in the medical image.

Figure 2:
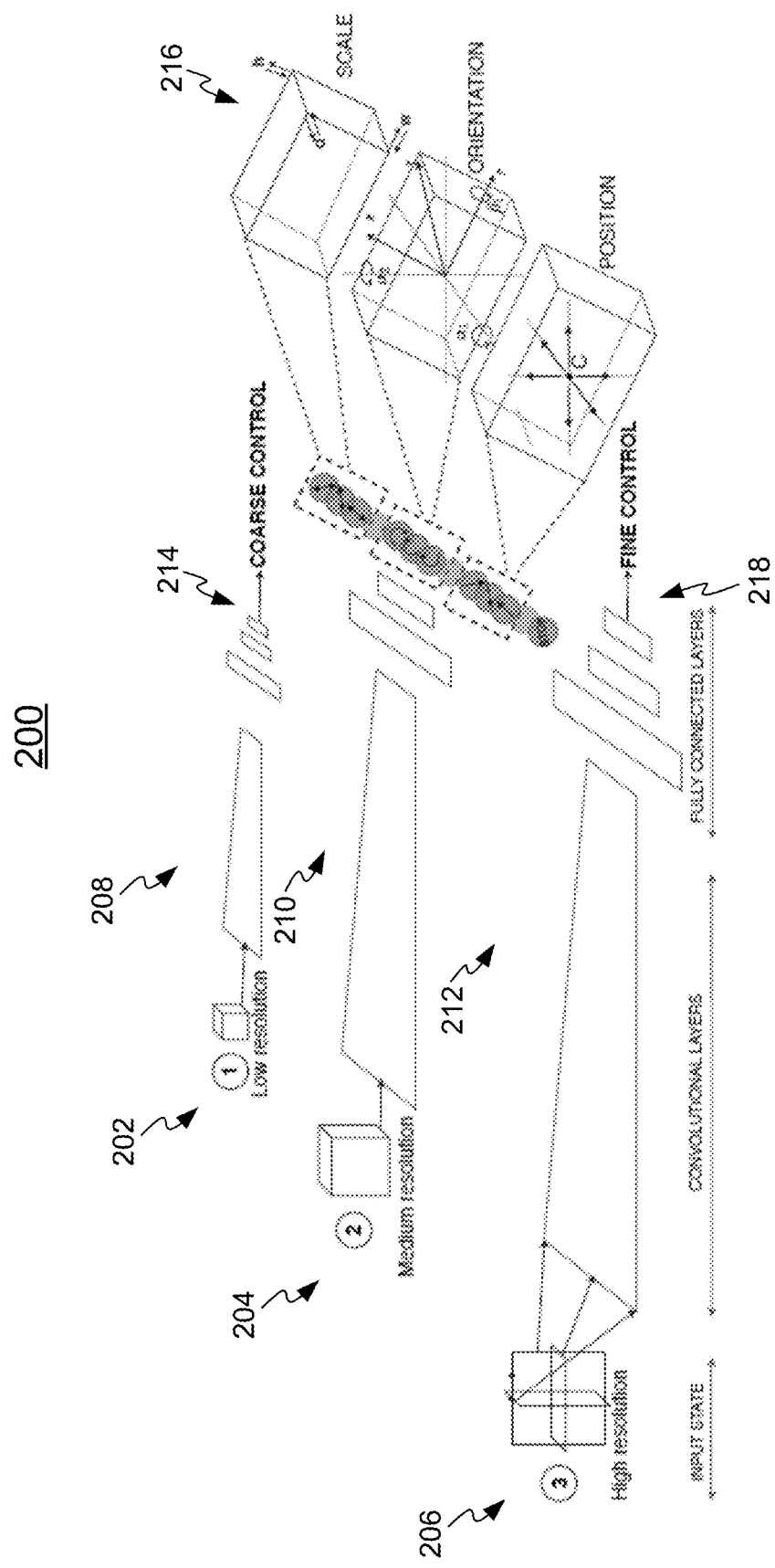
FIG. 2 shows a high-level framework for localizing a target object in a medical image, in accordance with one or more embodiments.

FIG. 2 shows a high-level framework 200 for localizing a target object in a medical image, in accordance with one embodiment. The target object is modeled as a set of D independent parameters $\{x_i\}_{i=1}^{D}$, where D is the number of dimensions. Reachable parameter values form a D-dimensional parametric space of the medical image where an instance is uniquely represented as a point of coordinates $(x_1, \ldots, x_D)$. The goal of localization is to locate the target object in the medical image, or equivalently to find parameters $x^* = (x_1^*, \ldots, x_D^*)$ of the target object in the D-dimensional parametric space of the medical image representing the location of the target object.

The D-dimensional parametric space is discretized into regular intervals in every dimension, giving the set of reachable positions by the AI agent. The problem is modeled as a Markov Decision Process (MDP), defined by a tuple of objects (S, A, p, R, γ), where S is the set of possible states s, A is the set of possible actions a of the AI agent, p is the transition probability distribution (i.e., the probability of arriving at the next state after the AI agent performs the action a at the current state s), R is the scalar reward function, and γ is the discount function. A trained AI agent is deployed to navigate the D-dimensional parametric space with the goal of reaching x*, the parameters of the target object, representing the location of the target object. The trained AI agent actively learns to cope with the uncertain environment (i.e., the medical image) by performing a sequence actions.

Sampling the parametric space introduces a tradeoff between accuracy and efficiency. Larger steps lead to faster convergence, but smaller steps allow for approximating the location of the target object with greater precision. Framework 200 employs a multi-scale progressive optimization approach, where an AI agent evolves in a sequence of parametric spaces with increasing resolutions both in terms of field-of-view and control.

In framework 200, the medical image is discretized (e.g., down sampled) into a plurality of discrete images of different scale levels or resolutions comprising: image 202 having low resolution, image 204 having medium resolution, and image 206 having high resolution. While the images are shown in FIG. 2 as three images having three different resolutions, it should be understood that any number of images having different resolutions may be employed. A separate AI agent is trained for each resolution of images 202, 204, and 206. Each AI agent is represented by convolutional and fully connected layers 208, 210, and 212, respectively. For each of the plurality of images, the D-dimensional parametric space is also discretized into a grid of constant scale cells $\Delta^{(i)} = (\Delta_1^{(i)}, \ldots, \Delta_D^{(i)})$, where $\Delta^{(i)}$ determines the precision of the AI agent control over the parameters.

A respective AI agent navigates through the parametric space of images 202, 204, and 206 in a hierarchical manner progressively increasing in resolution to estimate parameters x*—starting with image 202 having low resolution (i.e., a lowest resolution), progressing to image 204 having medium resolution (i.e., a next highest resolution), and further progressing to image 206 having high resolution (i.e., a highest resolution). Starting with image 202 having low resolution, an AI agent (trained for low resolution) is initialized with an initial set of parameters $x^0=(x_1^0, \ldots, x_D^0)$ representing the location of the target object in D dimensions. The initial set of parameters $x^0$ can, for example, be determined during training from average values over the training set.

The AI agent performs a sequence of actions for modifying the parameters to optimize (e.g., maximize) a reward function learned by the AI agent. The modified parameters 214 from image 202 is output from layers 208 of the AI agent, which is used as the initial parameters of the target object by an AI agent navigating the parametric space of image 204. Accordingly, an AI agent (trained for medium resolution) performs a sequence of actions for modifying the parameters 214 to optimize (e.g., maximize) a reward function learned by the AI agent. The modified parameters 216 from image 204 is output from layers 210 of the AI agent, which is used as the initial parameters of the target object by an AI agent navigating the parametric space of image 206. An AI agent (trained for high resolution) performs a sequence of actions for modifying the parameters 216 to optimize (e.g., maximize) a reward function learned by the AI agent. The modified parameters 218 from image 208 is output from layers 212 of the AI agent as the final parameter values of the target object. In one embodiment, the final parameter values are defined in terms linear and non-linear parameters: position (i.e., (x, y, z) Cartesian coordinates), orientation (i.e., yaw, pitch, and roll), and scale (width, depth, and height) to represent the localization of the target object.

FIG. 3 shows a method 300 for localizing a target object in a medical image, in accordance with one or more embodiments. Method 300 utilizes a plurality of trained AI agents trained during a prior training stage. Training of the AI agents is described in further detail below with respect to FIG. 5. In one embodiment, method 300 is performed by workstation 102 of FIG. 1.

At step 302, a medical image is discretized (e.g., represented) into a plurality of images having different resolutions. The medical image comprises the target object to be localized. The target object may be any object of interest to be localized, such as, e.g., an anatomical landmark or structure. In one embodiment, the medical image is a 3D CT medical image, however it should be understood that the medical image may be of any suitable modality or domain. The medical image may be directly received from a medical imaging system, such as, e.g., medical imaging system 104 of FIG. 1. Alternatively, the medical image may be received by loading a previously acquired medical image from a storage or memory of a computer system or receiving a medical image that has been transmitted from a remote computer system.

In one embodiment, the medical image is discretized by down sampling the medical image into the plurality of images having different resolutions. For example, the medical image may be down sampled into the plurality of images having increasing image resolutions $L_1, L_2, \ldots, L_N$ respectively.

At step 304, for each respective image of the plurality of images, starting from a first image (e.g., an image having a lowest resolution) and progressing to a last image (e.g., an image having a highest resolution) with the progression increasing in resolution, a sequence of actions is performed for modifying parameters of the target object in the respective image. The parameters of the target object may comprise linear and/or non-linear parameters. For example, in one embodiment, the parameters of the target object comprise translation, rotation, and scaling parameters defining a nine dimensional space. The sequence of actions comprises discrete actions determined by an AI agent trained for the resolution of the respective image to optimizes (e.g., maximize) a reward function. The sequence of actions may also include a stop action in which the parameters of the target object are unchanged. Step 304 is described in further detail below with respect to FIG. 4.

At step 306, the target object is localized in the medical image based on the modified parameters of the target object in the last image. For example, the localization of the target object may be the location of an anatomical bounding box defined by the modified parameters of the target object.

At step 308, results of the localization of the target object in the medical image are output. In one embodiment, the results of the localization of the target object can be output by displaying the results of the localization of the target object on a display device of a computer system, storing the results of the localization of the target object on a memory or storage of a computer system, or by transmitting the results of the localization of the target object to a remote computer system.

Figure 4:
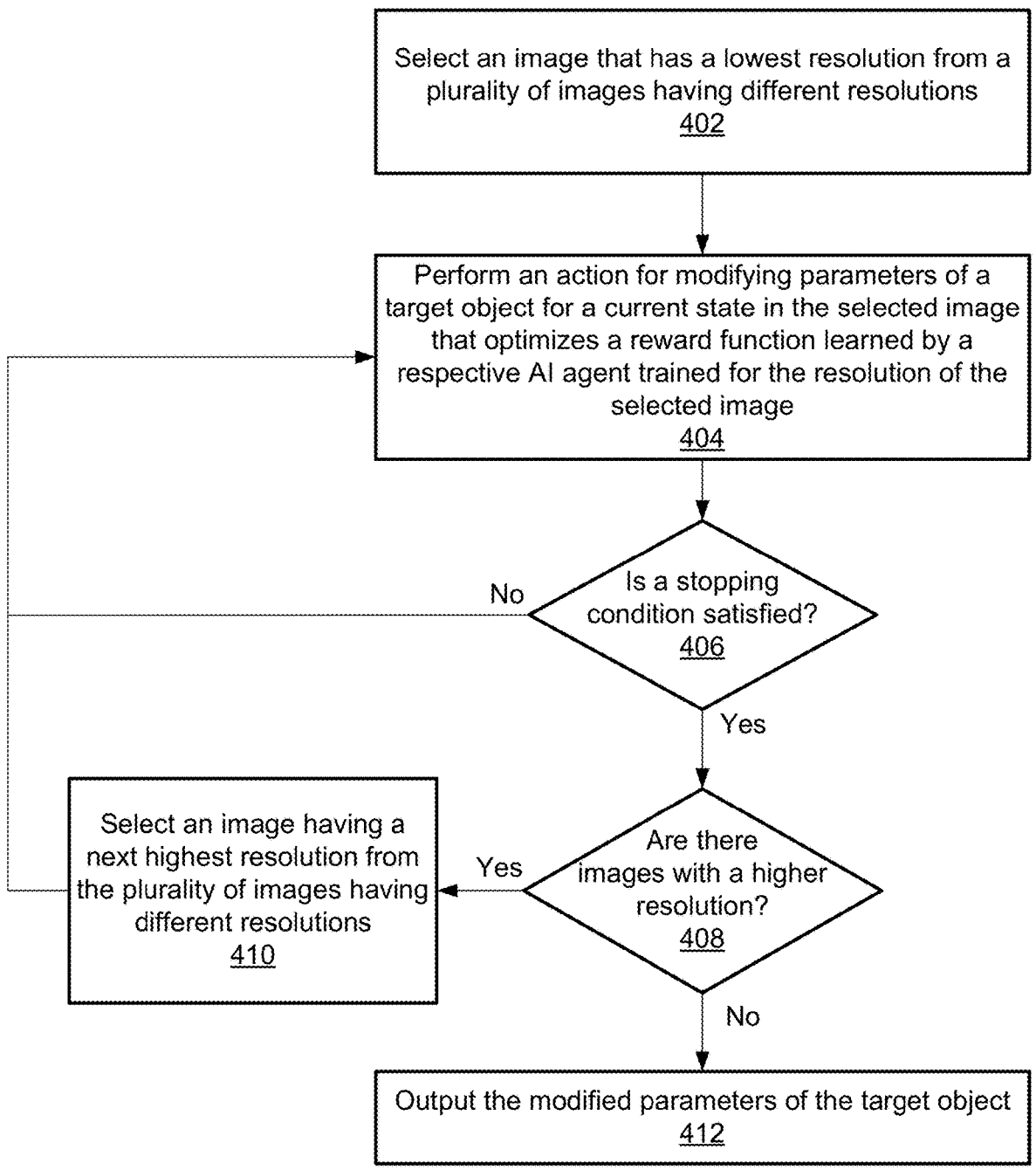
FIG. 4 shows a method for determining parameters of a target object for localizing the target object in a medical image, in accordance with one or more embodiments.

FIG. 4 shows a method 400 for determining parameters of a target object for localizing the target object in a medical image, in accordance with one or more embodiments. In one embodiment, method 400 may be performed at step 304 of FIG. 3.

At step 402, an image is selected that has a lowest resolution (i.e., a coarsest resolution) from a plurality of images having different resolutions.

At step 404, an action a is performed for modifying parameters of the target object for a current state $s_t$ in the selected image that optimizes a reward function r learned by a respective AI agent trained for the resolution of the selected image. The target object is initially defined by an initial set of parameters $x^0=(x_1^0, \ldots, x_D^0)$. Each respective AI agent is separately trained for the resolutions of each selected image during a prior training stage. Training of an AI agent is further described below with respect to FIG. 5.

Action a is determined from a plurality of actions available to the AI agent. There are (2D+1) actions available to the AI agent: 2D move actions and one stop action to terminate the search, where D is the number of dimensions. In one embodiment, there D=9 dimensions such that the plurality of move actions available to the AI agent comprising movement (in both the positive and negative direction): in the (x, y, z) Cartesian coordinates of the position of the target object; in the yaw, pitch, and roll of the orientation of the target object; and in the width, depth, and height of the scale of the target object. The movements of the AI agent in the parametric space are represented as unit-length steps along one of the basis vectors $(-e_1, +e_1, \ldots, -e_D, +e_D)$, where $e_D$ denotes the vector with a 1 in the dth coordinate and 0's elsewhere.

The current state $s_t$ at time step t represents the current visible region of the 3D environment (of the selected image) visible to the AI agent. The current state $s_t$ is the region of the current bounding box defined by the current parameters $x^t$ at step t plus a fixed margin of voxels to provide additional context. The AI agent receives the current state $s_t$ as a fixed-size grid of voxels. The current state $s_t$ is resampled at each time step.

The AI agent learns a reward function r as a strategy policy with the goal of optimizing (e.g., maximizing) a cumulative reward over one episode $R=\Sigma_{t=0}^{T}\gamma^{t}r_{t}$. A distance-based reward $r_t$ is defined as follows.

$$r_t = \begin{cases} dist(x_t, x^*) - dist(x_{t+1}, x^*) & \text{if } a_t \in \{1, \ldots, 2D\} \\ \left(\dfrac{dist(x_t, x^*) - d_{min}}{d_{max} - d_{min}} - 0.5\right) * 6 & \text{if } a_t = 2D+1 \\ -1 & \text{if } s_{t+1} \text{ is a non-legal state} \end{cases}$$

Where $dist(x_t,x')$ defines a distance metric between two objects x and x' in the parametric space. The rewards gives the agent an evaluative feedback each time it chooses an action $a_t$ from the current state $s_t$. The reward is positive when the AI agent gets closer to the ground truth target shape of the target object and negative otherwise. If one move action leads to a non-legal state $s_{t+1}$, the AI agent receives a negative reward −1. A state is non-legal state if one of the parameters is outside of a predefines allowed search range. If the agent decides to stop, the closer it is from the target the greater reward it gets and similarly, the further it is from the target the lesser reward it gets. The reward is bounded between [−1;1] for choosing a move action and between [−3;3] for the stop action. The distance metric may be any suitable distance metric. In some embodiments, the distance metrics may be the $l_p$-norm family, the intersection over union, or the average corner-to-corner distance.

At step 406, it is determined whether a stopping condition is satisfied. The stopping condition may be that the action at step 404 is a stop action, that two consecutive complementary actions (e.g., augmenting the width and reducing the width) were performed, that a predetermined maximum number of steps or iterations is satisfied, or any other suitable stopping condition.

If the stopping condition is not satisfied at step 406, then method 400 returns to step 404 and the AI agent performs another action by modifying parameters of the target object in the selected image. At a first step or iteration, action a is performed to modify the initial set of parameters $x^0$. At each subsequent step, action a is performed to modify the parameters modified at the prior step. Steps 404 is iteratively repeated for the selected image until the stopping condition is satisfied (step 406) to perform a sequence of actions for modifying parameters of the target object in the selected image.

If the stopping condition is satisfied at step 406, then at step 408 it is determined whether there are any images that have a higher resolution than the selected image in the plurality of images having different resolutions. If there are images with a higher resolution than the selected image, at step 410, an image having a next highest resolution is selected from the plurality of images having different resolutions. Method 400 then returns to step 404 using the image having the next highest resolution as the selected image to determine an action for modifying parameters of a target object in the image having the next highest resolution. The modified parameters of the target object determined for a selected image are used as the initial parameters of the target object for the next selected image (i.e., the image having the next highest resolution).

Steps 404 and 406 are iteratively repeated for each selected image (i.e., each image in the plurality of images having different resolutions) until the stopping condition is satisfied (step 406) to determine a sequence of actions for modifying parameters of the target object in the selected image based on a respective AI agent trained for the resolution of the selected image. In this manner, a sequence of actions for transforming an anatomical bounding box, defined by the modified parameters of the target object, are hierarchically performed for each of the plurality of images having different resolutions, starting from the image having a lowest resolution (i.e., a coarsest resolution) to an imaging having a highest resolution (i.e., a finest resolution). Such a multi-scale progressive control strategy provides greater computational efficiency.

At step 412, the final modified parameters of the target object (determined from the image having a highest resolution) is output. For example, the modified parameters of the target object box may be output by displaying an anatomical bounding box defined according to the modified parameters of the target object, storing the modified parameters on a memory or storage of a computer system, or by transmitting the modified parameters to a remote computer system.

Figure 5:
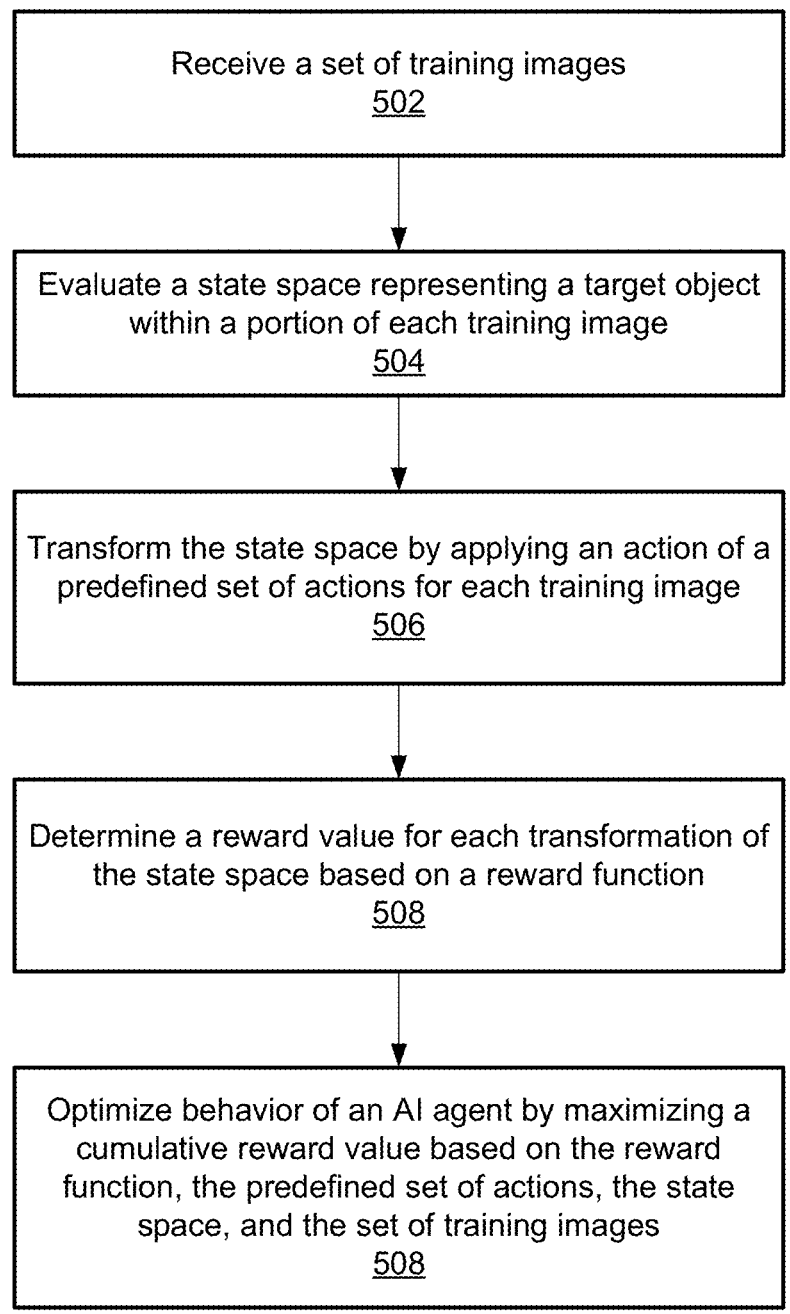
FIG. 5 shows a method for training an artificial intelligence agent for localizing a target object in a medical image, in accordance with one or more embodiments.

FIG. 5 shows a method 500 for training an AI agent for modifying parameters of a target object to localize the target object in a medical image, in accordance with one or more embodiments. The steps of method 500 may be repeatedly performed to train a plurality of AI agents each corresponding to a different resolution. Method 500 is performed to train one or more AI agents during a training stage. Once trained, the one or more trained AI agents may be applied during an online or inference stage, such as, e.g., method 300 of FIG. 3 or method 400 of FIG. 4.

During training, the AI agent learns a policy indicating which action to take for a given state. The AI agent gradually learns how to adapt its current policy until it finds the optimal policy returning a sequence of actions optimizing the cumulative discounted reward R from a given start state $s_0$. The AI agent is trained using deep reinforcement learning (e.g., Q-learning) combined with a neural network function approximator due to the lack of prior knowledge about the state-transition and the reward probability distributions (model-free setting) and due to the high-dimensionality of the input date (continuous volumetric images). The optimal action-value function is estimated using a deep Q-network (DQN): $Q^*(s,a) \approx Q(s, a, \theta)$. Q-learning is used to update the network by minimizing a sequence of loss functions $L_i(\theta_i)$ expressing how far $Q(s, a; \theta_i)$ is from its target $y_i$: $L_i(\theta_i) = \mathbb{E}_{s,a,r,s}(y_i - Q(s, a; \theta_i))^2$. For effective training of the DQN, the concepts of experience replay, ϵ-greedy exploration, and loss clipping are incorporated. The actions during training are constrained to the positive direction (i.e., actions leading to a positive reward) to accelerate the AI agent's discovery of positive reward trajectory.

At step 502, a set of training images is received. The training images in the set have a resolution corresponding to the resolution for which the AI agent is to be trained. The training images are annotated to identify a location of a target object.

At step 504, a state space representing an anatomical bounding box defining a localization of a target object is evaluated within a portion of each training image.

At step 506, the state space is transformed by applying an action of a predefined set of actions for each training image. In one embodiment, the predefined set of actions comprises move actions in the (x, y, z) Cartesian coordinates of the position of the bounding box; in the yaw, pitch, and roll of the orientation of the bounding box; and in the width, depth, and height of the scale of the bounding box; and a stop action in which the bounding box is unchanged.

At step 508, a reward value is determined for each transformation of the state space. The reward value is based on a distance of the current state space to the target object.

At step 510, the behavior of the AI agent is optimized by maximizing a cumulative reward value based on the reward value, the predefined set of actions, the state space, and the set of training images. The AI agent thereby learns to determine the most favorable sequence of actions to localize a target object.

Embodiments of the present invention were experimentally validated. MRI scans of the head region were acquired to localize a standard box from scout or localizer images that cover the brain. This is a challenging task requiring robustness against variations in the localizer scan orientation, the view of the object, and the brain anatomy. In some cases, some of the brain or bone structures may be missing or displaced either by natural development or by pathology.

The dataset consisted of 530 annotated MRI scans of the head region. 500 scans were used for training and 30 for testing. The 30 test cases were annotated twice by different experts to compute the inter-rater variability. 15 additional challenging test cases with pathologies (tumors or fluid swelling in brain tissue), in plane rotation of the head, thick cushion of the head rest, or cropped top of the skull were selected to evaluate the robustness of the disclosed embodiments.

The scale space of the images was discretized into 4 levels: 16 mm ($L_1$), 8 mm ($L_2$), 4 mm ($L_3$), and 2 mm ($L_4$). The images, or input resolution (1.6×1.5625×1.5625) were isotropically down sampled to 16, 8, 4, and 2 mm. The voxel intensities were clipped between the $3^{rd}$ and $97^{th}$ percentile and normalized to the [0;1] range.

Ground truth boxes were annotated based on anatomical structures present in the brain region. The orientation of the box is determined by positioning the brain midsagittal plane (MSP), separating the two brain hemispheres, and going through the Crista Galli, Sylvian Aqueduct, and Medulla Oblongata. The rotational alignment within the MSP is based on two anatomical points: the inflection distinguishing the Corpus Callosum (CC) Genu from the CC Rostrum and the most inferior point on the CC Splenium. Given this orientation, the lower margin of the box is defined to intersect the center of C1-vertebrae arches points. The other box extremities define an enclosing bounding box of the brain.

Following the annotation protocol, an orthonormal basis (i, j, k) is defined, where i is the normal of the MSP and j defines the rotation within the MSP. The orientation of the box is controlled by three angles: $\alpha_1$ and $\alpha_2$, which control the yaw and pitch of the MSP respectively, and $\beta_1$, which controls the inplane roll around i. The center position is parameterized by its Cartesian coordinates $C=(C_x, C_y, C_{z'})$. The scale is parameterized by the width w, depth d, and height h of the box.

During the experiments, the first box is set to cover the whole image at the coarsest scale and is sequentially refined following decisions of the AI agent. FIG. 6 shows a table 600 comparing the inventive approach, in accordance with embodiments of the present invention, human performance (inter-rater variability), and a conventional landmark-based method.

The landmark-based method detects 14 landmarks carefully chosen after box definition. The midsagittal plane is consequently initialized with random sample consensus (RANSAC) robust fitting. Finally, a box is fitted with a gradient descent algorithm to minimize angular and positional errors with respect to the detected landmarks. 8 out of 14 landmarks are associated with the angles $\alpha_1$ and $\alpha_2$, therefore achieving good results for these measures. On the other hand, due to the fewer landmarks associated with $\beta_1$, this angle is not robust to outliers.

The inventive approach achieves performances in the range of the inter-observer variability (human performance) for every measure. Performing a direct optimization on the box parameters, the inventive approach does not rely on the previous detection of specific points. For recall, the finer scale level is set of 2 mm, meaning that the inventive approach achieves an average accuracy of 1-2 voxels precision. Major failures were not observed over the 15 difficult test cases, showing robustness to diverse image acquisitions, patient orientations, brain anatomy, and extreme clinical cases.

During the inference stage, the inventive approach runs in 0.6 seconds on average on a GeForce GTX graphics processing unit. This processing time includes the navigation of the 4 scale levels. If near real-time performance is desired, the search can be stopped at 4 mm resolution with minor loss in accuracy, reducing the average runtime to less than 0.15 seconds.

Figure 7:
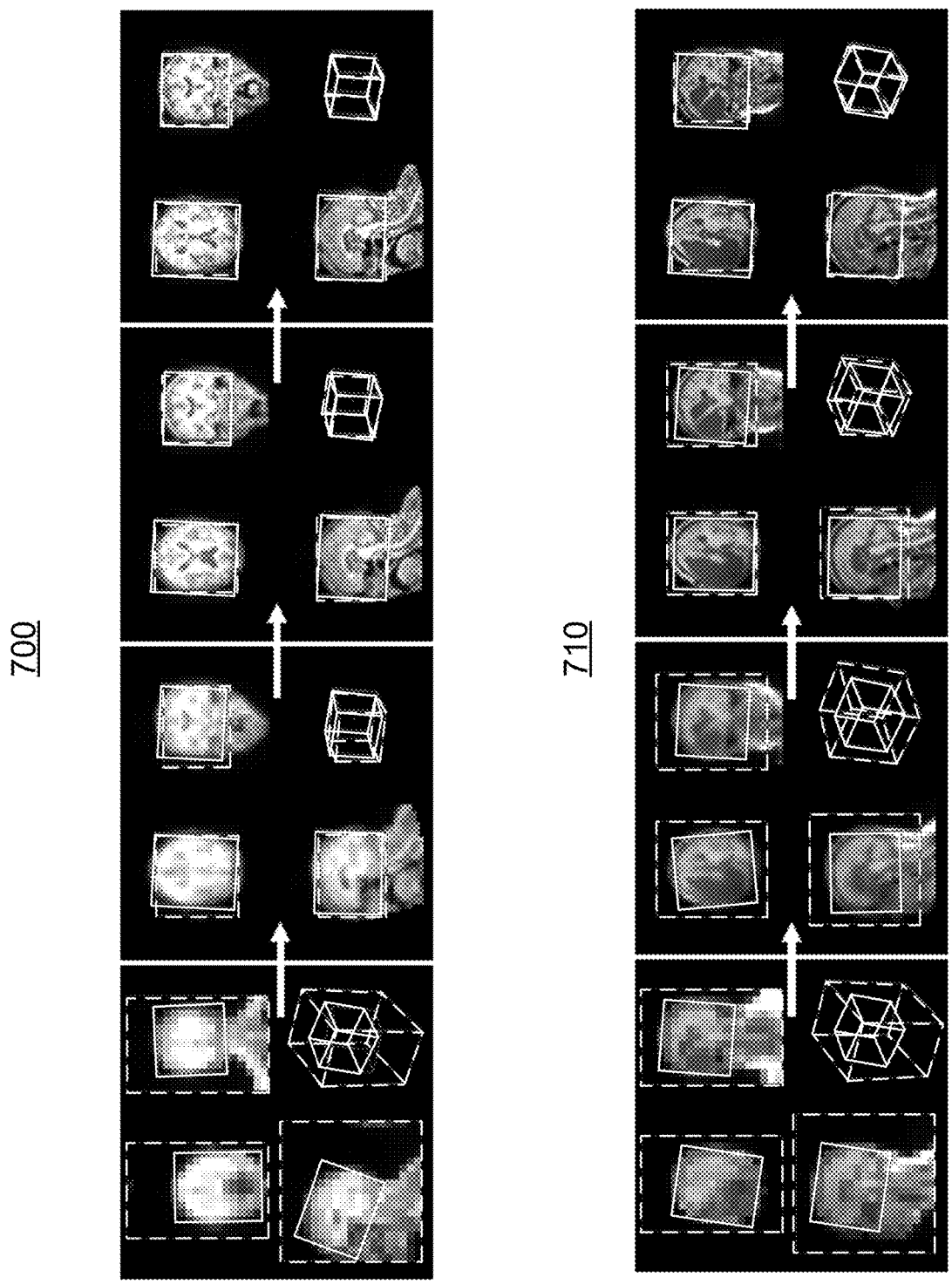
FIG. 7 shows a sequence of images comparing embodiments of the present invention with conventional methods.

FIG. 7 shows a sequences of images 700 and 710 comparing a current bounding box (shown in dashed lines) determined in accordance with embodiments of the present invention with ground truths (shown in solid lines). Each image in sequences 700 and 710 depicts the bounding box refined using images of increasing resolution.

To implement the experiment, the step length at each scale level $L_i$ (resolution $2^{4-i}$ mm) was fixed as follows:

$$\Delta C_x = \Delta C_y = \Delta C_z = 2^{4-i} \text{mm};$$

$$\Delta w = \Delta d = \Delta h = 2^{4-i} \text{mm};$$

$$\Delta \alpha_1 = \Delta \alpha_2 = \frac{1}{2} a\cos\left(\frac{\overline{w}/2^{4-i}}{\sqrt{(\overline{w}/2^{4-i})^2 + 1}}\right) \text{degrees; and}$$

$$\Delta \beta_1 = \frac{1}{2} a\cos\left(\frac{\overline{d}/2^{4-i}}{\sqrt{(\overline{d}/2^{4-i})^2 + 1}}\right) \text{degress}.$$

$\overline{w}$ and $\overline{d}$ are the mean box width and depth in mm, respectively. The AI agent can control the box position and size at 1 voxel precision, and the box orientation by rotating the box extremities of a half a voxel precision.

The dimension of the input grid of voxels s is set to $25^3$ voxels for $L \in \{L_1, L_2\}$ and to $50^3$ voxels for $L_3$, in order to contain the whole box at the current spatial sampling density. For computational efficiency, only the central orthogonal planes of the box are warped to three 90×90×5 input grids of voxels for $L_4$.

For the reward, the actions are clustered into three groups (translation, rotation, and scaling). The $l_2$-norm is used as the distance metric:

$$dist(x, x') = \begin{cases} (1)\sqrt{\varsigma x_{x \to x'}^2 + \varsigma y_{x \to x'}^2 + \varsigma z_{x \to x'}^2} & \text{if } a_t \in \text{translation} \\ (2)\sqrt{\varsigma \alpha_{1_{x \to x'}}^2 + \varsigma \alpha_{2_{x \to x'}}^2 + \varsigma \alpha_{3_{2_{x \to x'}}}^2} & \text{if } a_t \in \text{rotation} \\ (3)\sqrt{\varsigma w_{x \to x'}^2 + \varsigma d_{x \to x'}^2 + \varsigma h_{x \to x'}^2} & \text{if } a_t \in \text{scaling} \\ (1) + (2) + (3) & \text{if } a_t \in \text{stop} \end{cases}$$

For the coarse scale, a state is not legal either if the center position is outside of the image boundaries, or if the box size is greater than 1.5 times the image dimensions or if the angle between the box (i,j) vectors and the image (x,y) axis are greater than (30°,60°) respectively. For the other scales, the search-range is constrained to ±10 steps around the reference ground truth box.

The models $Q(\theta_1)$, $\theta(\theta_2)$, $Q(\theta_3)$ and $Q(\theta_4)$ are independently trained for each scale level. The networks are composed of three 3D convolutional layers (32 kernels, stride 2, batch normalization and ReLU) followed by three fully-connected layers (256, 128, 19 units, ReLU). For 16, 8, and 4 mm, the convolutional kernels and stride sizes are isotropic. For 2 mm, the three planar inputs are processed by three parallel branches of convolutional layers with planar kernels and stride sizes. The resulting feature maps are concatenated before going through the fully-connected block.

The models are trained for 100 epochs, one epoch lasts 1500 agent steps. The episode length is linearly decayed from 1500 to 15. ε is linearly annealed from 1.0 to 0.1 during the first 100 epochs and then fixed to 0.1. The replay memory can store 10,000 transitions (s, a, r, s'). The training starts after 5,000 random steps with one training step for each 10 agent step. The target network used in the DDQN loss term is updated every 5,000 steps. Root mean square (RMS)-prop optimizer is used with $\propto=0.0005$, $\rho=0.95$, and $\in=0.01$. The mini batch size is set to 256 for $L_1$ and $L_2$ scale levels, to 128 for $L_3$, and to 64 for $L_4$. All experiments were performed on the PyTorch platform.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps of FIGS. 3-5. Certain steps of the methods and workflows described herein, including one or more of the steps of FIGS. 3-5, may be performed by a server or by another processor in a network-based cloud-computing system. Certain steps or functions of the methods and workflows described herein, including one or more of the steps of FIGS. 3-5, may be performed by a client computer in a network-based cloud computing system. The steps or functions of the methods and workflows described herein, including one or more of the steps of FIGS. 3-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 3-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 8:
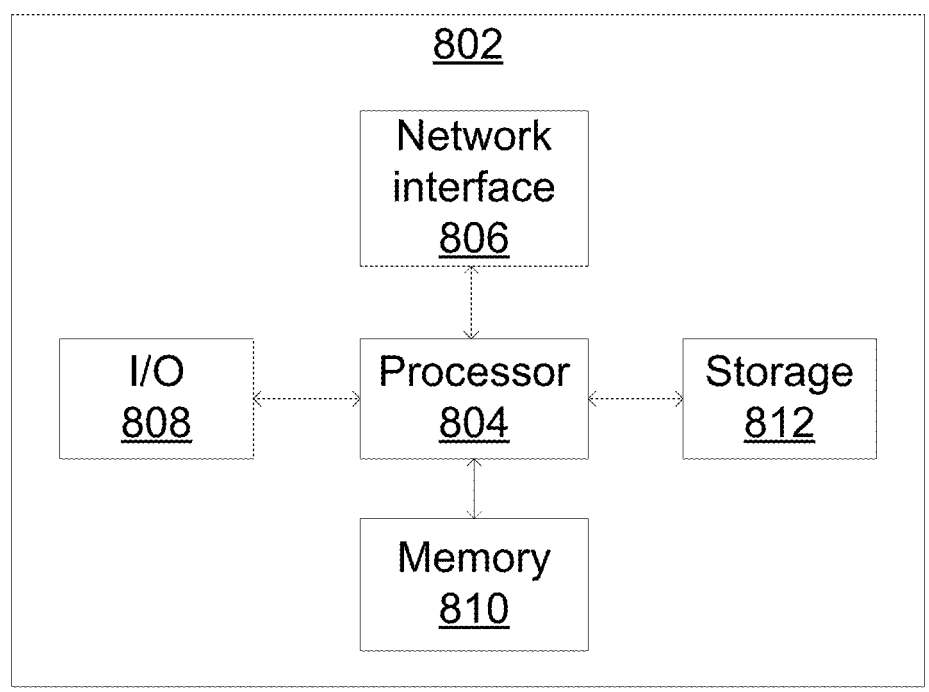
FIG. 8 shows a high-level block diagram of a computer.

A high-level block diagram of an example computer 802 that may be used to implement systems, apparatus, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps of FIGS. 3-5 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps or functions of FIGS. 3-5. Accordingly, by executing the computer program instructions, the processor 804 executes the method and workflow steps of FIGS. 3-5. Computer 804 may also include one or more network interfaces 806 for communicating with other devices via a network. Computer 802 may also include one or more input/output devices 808 that enable user interaction with computer 802 (e.g., display, keyboard, mouse, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

Any or all of the systems and apparatus discussed herein, including elements of workstation 102 of FIG. 1, may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for localizing a target object in a medical image, comprising:
   discretizing the medical image into a plurality of images having different resolutions;
   for each respective image of the plurality of images, starting from a first image and progressing to a last image with the progression increasing in resolution, performing a sequence of actions for modifying parameters of the target object in the respective image, the parameters of the target object comprising nonlinear parameters of the target object, wherein each of the sequences of actions is determined to optimize a reward function by an artificial intelligence (AI) agent of a plurality of AI agents each separately trained for a corresponding one of the resolutions of the plurality of images; and
   localizing the target object in the medical image based on the modified parameters of the target object in the last image.

2. The method of claim 1, wherein the parameters of the target object comprise translation, rotation, and scaling parameters defining a nine dimensional space.

3. The method of claim 1, wherein the AI agent is trained using deep reinforcement learning.

4. The method of claim 1, wherein the sequence of actions comprise a stop action in which the parameters of the target object are unchanged.

5. The method of claim 1, wherein the modified parameters of the target object in the respective image are used as initial parameters for the target object in a next image in the plurality of images.

6. The method of claim 1, wherein performing a sequence of actions for modifying parameters of the target object in the respective image comprises:
   repeatedly performing an action for modifying the parameters of the target object for a current state in the respective image that optimizes the reward function learned by the AI agent trained for the resolution of the respective image until a stopping condition is satisfied.

7. The method of claim 6, wherein the stopping condition comprises one of a stop action determined by the AI agent, a predetermined number of steps, and consecutive complementary actions.

8. The method of claim 1, wherein the target object is an anatomical landmark.

9. An apparatus for localizing a target object in a medical image, comprising:
   means for discretizing the medical image into a plurality of images having different resolutions;
   means for, for each respective image of the plurality of images, starting from a first image and progressing to a last image with the progression increasing in resolution, performing a sequence of actions for modifying parameters of the target object in the respective image, the parameters of the target object comprising nonlinear parameters of the target object, wherein each of the sequences of actions is determined to optimize a reward function by an artificial intelligence (AI) agent of a plurality of AI agents each separately trained for a corresponding one of the resolutions of the plurality of images; and
   means for localizing the target object in the medical image based on the modified parameters of the target object in the last image.

10. The apparatus of claim 9, wherein the parameters of the target object comprise translation, rotation, and scaling parameters defining a nine dimensional space.

11. The apparatus of claim 9, wherein the AI agent is trained using deep reinforcement learning.

12. The apparatus of claim 9, wherein the modified parameters of the target object in the respective image are used as initial parameters for the target object in a next image in the plurality of images.

13. The apparatus of claim 9, wherein the means for performing a sequence of actions for modifying parameters of the target object in the respective image comprises:
   means for repeatedly performing an action for modifying the parameters of the target object for a current state in the respective image that optimizes the reward function learned by the AI agent trained for the resolution of the respective image until a stopping condition is satisfied.

14. The apparatus of claim 13, wherein the stopping condition comprises one of a stop action determined by the AI agent, a predetermined number of steps, and consecutive complementary actions.

15. A non-transitory computer readable medium storing computer program instructions for localizing a target object in a medical image, the computer program instructions when executed by a processor cause the processor to perform operations comprising:
   discretizing the medical image into a plurality of images having different resolutions;
   for each respective image of the plurality of images, starting from a first image and progressing to a last image with the progression increasing in resolution, performing a sequence of actions for modifying parameters of the target object in the respective image, the parameters of the target object comprising nonlinear parameters of the target object, wherein each of the sequences of actions is determined to optimize a reward function by an artificial intelligence (AI) agent of a plurality of AI agents each separately trained for a corresponding one of the resolutions of the plurality of images; and localizing the target object in the medical image based on the modified parameters of the target object in the last image.

16. The non-transitory computer readable medium of claim 15, wherein the parameters of the target object comprise translation, rotation, and scaling parameters defining a nine dimensional space.

17. The non-transitory computer readable medium of claim 15, wherein the AI agent is trained using deep reinforcement learning.

18. The non-transitory computer readable medium of claim 15, wherein the sequence of actions comprise a stop action in which the parameters of the target object are unchanged.

19. The non-transitory computer readable medium of claim 15, wherein the modified parameters of the target object in the respective image are used as initial parameters for the target object in a next image in the plurality of images.

20. The non-transitory computer readable medium of claim 15, wherein the target object is an anatomical landmark.

* * * * *